US012648706B2

(12) United States Patent
Yang et al.

(10) Patent No.: US 12,648,706 B2
(45) Date of Patent: Jun. 9, 2026

(54) STEERABLE AND ADJUSTABLE RECORDER PULSE PILLOW FOR TRADITIONAL CHINESE MEDICINE PULSE DIAGNOSIS

(71) Applicant: Institute of Information on Traditional Chinese Medicine, China Academy of Chinese Medical Sciences, Beijing (CN)

(72) Inventors: Jie Yang, Beijing (CN); Baoyan Liu, Beijing (CN); Tiancai Wen, Beijing (CN); Bin Wang, Beijing (CN); Lei Zhang, Beijing (CN)

(73) Assignee: Institute of Information on Traditional Chinese Medicine, China Academy of Chinese of Medical Sciences, Beijing (CN)

( * ) Notice: Subject to any disclaimer, the term of this patent is extended or adjusted under 35 U.S.C. 154(b) by 630 days.

(21) Appl. No.: 18/124,616

(22) Filed: Mar. 22, 2023

(65) Prior Publication Data

US 2023/0301534 A1     Sep. 28, 2023

(30) Foreign Application Priority Data

Mar. 22, 2022    (CN) .......................... 202210287179.8

(51) Int. Cl.
*A61B 5/0255* (2006.01)
*A61B 5/00* (2006.01)

(52) U.S. Cl.
CPC .......... *A61B 5/0255* (2013.01); *A61B 5/6824* (2013.01); *A61B 5/6892* (2013.01); *A61B 5/742* (2013.01)

(58) Field of Classification Search
CPC ... A61B 5/01; A61B 5/02055; A61B 5/02108; A61B 5/0255; A61B 5/0803;
(Continued)

(56) References Cited

U.S. PATENT DOCUMENTS 6,210,340 B1 *   4/2001   Amano ................ A61B 5/6838
                                                          600/500
2012/0184860 A1 *   7/2012   Pan ........................ A61B 5/684
                                                          600/500
(Continued)

FOREIGN PATENT DOCUMENTS

CN            106667455 A  *  5/2017   ............... A61B 5/02
CN            106913319 A  *  7/2017   ............... A61B 5/02
(Continued)

OTHER PUBLICATIONS

CN-106667455-A English Translation (Year: 2017).*
(Continued)

*Primary Examiner* — Aurelie H Tu
*Assistant Examiner* — Andrew E Hoffpauir
(74) *Attorney, Agent, or Firm* — HOWARD M COHN and Associates, LLC

(57) ABSTRACT

The present disclosure provides a steerable and adjustable recorder pulse pillow for Traditional Chinese Medicine pulse diagnosis, and relates to the technical field of recorder pulse pillows. The steerable and adjustable recorder pulse pillow for Traditional Chinese Medicine pulse diagnosis comprises a main body, wherein a platform is installed right above the main body. The top surface of the platform is installed with a recording device. The bottom of the recording device is provided with a rotary disc. The rear end surface of the recording device is provided with an operating button. The rotary disc is fixedly connected with a micro-motor driving wheel inside the recording device. The micro-motor is electrically connected with a rotary knob of the recording device.

10 Claims, 5 Drawing Sheets

(58) Field of Classification Search
CPC ..... A61B 5/333; A61B 5/4854; A61B 5/6824; A61B 5/6892; A61B 5/702; A61B 5/742; A62B 2560/02; A62B 2560/0295
See application file for complete search history.

(56) References Cited

U.S. PATENT DOCUMENTS

| | | | | |
|---|---|---|---|---|
| 2014/0323886 A1* | 10/2014 | Lee | ....................... | A61B 5/0255 |
| | | | | 600/500 |
| 2015/0190065 A1* | 7/2015 | Kim | ................... | A61B 5/02427 |
| | | | | 600/479 |
| 2021/0228102 A1* | 7/2021 | Li | .......................... | A61B 5/681 |

FOREIGN PATENT DOCUMENTS

| | | | | | |
|---|---|---|---|---|---|
| CN | 206910509 U | * | 1/2018 | | |
| CN | 108078553 A | * | 5/2018 | ............... | A61B 5/02 |
| CN | 108523859 A | * | 9/2018 | ............... | A61B 5/02 |
| CN | 108968930 A | * | 12/2018 | ............... | A61B 5/02 |
| CN | 109124596 A | * | 1/2019 | ............ | A61B 90/00 |
| CN | 208355448 U | * | 1/2019 | | |
| CN | 109549630 A | * | 4/2019 | ........... | A61B 5/4854 |
| CN | 109924954 A | * | 6/2019 | | |
| CN | 113440113 A | * | 9/2021 | .......... | A61B 5/6824 |
| CN | 215457949 U | * | 1/2022 | | |
| CN | 215502968 U | * | 1/2022 | | |
| EP | 1360930 A1 | * | 11/2003 | ............... | A61B 5/02 |

OTHER PUBLICATIONS

CN-109924954-A English Translation (Year: 2019).*
CN-206910509-U English Translation (Year: 2018).*
CN-106913319-A English Translation (Year: 2017).*
CN-109124596-A English Translation (Year: 2019).*
CN-108968930-A English Translation (Year: 2018).*
CN-108078553-A English Translation (Year: 2018).*
CN-108523859-A English Translation (Year: 2018).*
CN-208355448-U (Year: 2019).*
CN-109549630-A (Year: 2019).*
CN-215457949-U (Year: 2022).*
CN-215502968-U (Year: 2022).*
CN-113440113-A (Year: 2021).*

* cited by examiner

A

B

C

STEERABLE AND ADJUSTABLE RECORDER PULSE PILLOW FOR TRADITIONAL CHINESE MEDICINE PULSE DIAGNOSIS

CROSS REFERENCE

This application is based upon and claims priority benefits to Chinese Patent Application No. 202210287179.8, filed on Mar. 22, 2022, the contents of which are incorporated herein by reference.

TECHNICAL FIELD

The present disclosure relates to the technical field of pulse pillows, in particular to a steerable and adjustable recorder pulse pillow for Traditional Chinese Medicine pulse diagnosis.

BACKGROUND

In the diagnosis of Traditional Chinese Medicine, there are four steps of diagnosis, that is, inspecting, listening, questioning and feeling. As a way of pulse diagnosis, feeling is the most important step, which is used to judge the disease condition of a patient. In the process of pulse diagnosis, in order to place the wrist of the patient flatwise and make the patient have a certain degree of comfort, a pulse pillow is an indispensable appliance, and a recorder can provide functions of recording and storing information, which is convenient for doctors to store information such as clinical history and physical sign of patients and can be used as an auxiliary device to help pulse diagnosis.

However, at present, most of the traditional recorder pulse pillows have a fixed structure and are placed on a desktop. A recorder only provides a doctor with a visual angle, which is inconvenient to steer and adjust and let the patient watch his own physical sign information. A pulse pillow only provides a cushion at the wrist for patients, but the body features of children, adults, men and women are different. The arm support depends on the desktop, and the position of the pulse pillow needs to be adjusted at any time. It is inconvenient for different people to use the pulse pillow. Moreover, the pulse pillow occupies the use space of the desktop in use, and the pulse pillow cannot provide functions such as temperature measurement, so that the temperature of patients cannot be judged during pulse diagnosis.

SUMMARY

In view of this, the present disclosure provides a steerable and adjustable recorder pulse pillow for Traditional Chinese Medicine pulse diagnosis, which has a recording device. The direction of the rotary disc can be adjusted by an operating button to realize angle adjustment, which is convenient for patients to watch their information.

The present disclosure provides a steerable and adjustable recorder pulse pillow for Traditional Chinese Medicine pulse diagnosis, specifically comprising a main body, wherein a pulse pillow is placed above the main body, a platform is installed right above the main body, a pallet assembly is movably connected inside the main body, a fastener is fixedly connected to the right end of the main body, a moving device is fixedly connected to the bottom surface of the main body; the platform has a rectangular structure and has a recording device installed on the top surface; the bottom of the recording device is provided with a rotary disc, the rear end surface of the recording device is provided with an operating button, the rotary disc is fixedly connected with a micro-motor driving wheel inside the recording device, the micro-motor is electrically connected with a rotary knob of the recording device, and the bottom of the recording device is movably clamped with a rotating wheel; the bottom of the rotating wheel is fixedly connected with a connecting cover; the connecting cover is internally clamped with a clamping band and a protection ring; a connecting plate included in the moving device is fixedly connected to the bottom surface of the pallet assembly, a driving block included in the moving device is fixedly connected to the bottom surface of the main body, a driver is installed at the rear end of the driving block, the driver is electrically connected with the operating button of the recording device; the left end of the fastener is fixedly connected with a bearing plate and a sliding rail, the left end of the bearing plate is fixedly connected with a rotating pipe, and the left side of the sliding rail is slidably clamped with the pressing block.

Preferably, the main body comprises a support rod and a drawer, the support rod is fixed and vertically connected to the top surface of the main body, the top surface of the support rod is fixedly connected to the bottom surface of the platform, and the drawer is movably clamped in the main body.

Preferably, the pallet assembly consists of a connecting pallet and a moving pallet, and has three groups of connecting pallets with the same structure, the rear end surface of each connecting pallet and the moving pallet is fixedly connected with towbars with I-shaped structures, respectively, the rear end of the bottom surface of the connecting pallet is fixedly connected with an abutting plate, the middle longitudinal beam of the towbar penetrates through the abutting plate, and the rear cross beam of the towbar is clamped at the rear side of the abutting plate.

Preferably, the top surface of the recording device is provided with a display screen, the display screen is connected with a PLC controller and a CPU chip circuit inside the recording device, and the display screen is electrically connected with the operating button.

Preferably, the rotating wheel comprises a driving wheel, the driving wheel has a bevel gear structure and is movably clamped at the bottom of the rotating wheel, and the driving wheel is coaxially and fixedly connected with the rotating wheel.

Preferably, the connecting cover comprises an adjusting wheel, a clamping groove and a mounting groove, the adjusting wheel has a bevel gear structure and is meshed with the driving wheel, the outside of the clamping groove has an 8-shaped structure and the inside of the clamping groove is installed with a clamping band, the mounting groove is provided below the clamping groove, and the inside of the mounting groove is clamped with the protection ring.

Preferably, a clamping strip is provided at the outer side of the end of the clamping band, the clamping strip is meshed with the adjusting wheel, the inner side surface of the clamping band is attached to the outer side surface of the protection ring, and the clamping band is the cold end of a thermocouple thermometer and is communicated with the internal working end of the recording device.

Preferably, the moving device further comprises a telescopic rod and a fixed block, the front end of the telescopic rod is fixedly connected with the front end surface of the connecting plate, the rear end of the telescopic rod is fixedly connected with the driving block, the periphery of the rear side of the telescopic rod is fixedly connected with the fixed block, and the top surface of the fixed block is fixedly connected with the bottom surface of the main body through a bolt assembly.

Preferably, the left end of the fastener is further provided with a fastening pipe, the fastening pipe has a threaded sleeve structure, the outer pipe at the upper end of the fastening pipe is movably clamped at the upper end of the left side of the fastener, the inner pipe at the lower end of the fastening pipe is movably clamped with a pressing plate, and the pressing plate has a right-angle structure and is movably clamped to the left side of the sliding rail.

Preferably, the rotating pipe comprises a threaded pipe, the threaded pipe is movably connected in the rotating pipe through threaded engagement, and the top surface of the threaded pipe is movably clamped in the pressing block.

Beneficial Effects

Compared with the traditional recorder pulse pillow, for the recorder pulse pillow according to each embodiment of the present disclosure, after a recording device records the physical sign information such as body temperature, pulse, and heart rate of a patient, the information is recorded and stored through the operating button, and a real-time picture is displayed through a display screen. The rotating direction and angle of the micro-motor can be adjusted by the rotary knob according to the sitting position of a patient, and the rotating angle of the recording device is then driven through the rotary disc, so that the patient can watch the information displayed on the picture of the display screen through steering adjustment.

In addition, when the moving pallet moves forward and stretches, the towbar on the bottom surface of the moving pallet is driven to move forward and slide inside a group of adjacent abutting plates at the bottom surface of the connecting pallet. After the towbar moves to the rear cross beam and abuts against the rear end surface of the abutting plate, the towbar drives the abutting plate to move and also drives the connecting pallet to move forward, so as to finally complete the stretch of the pallet assembly. When the moving pallet moves backward and folds, the towbar at the bottom surface of the moving pallet is driven to move backward and slide inside a group of adjacent abutting plates at the bottom surface of the connecting pallet. After the front cross beam of the towbar abuts against the front end surface of the abutting plate, the towbar drives the abutting plate to move backward and also drives the connecting pallet to move backward, so as to finally complete the folding of the pallet assembly, which is convenient for different people to support their arms.

In addition, after the fastening pipe is rotated, the inner pipe at the lower end is driven to rotate and move, and the pressing plate is driven to slide on the left side of the sliding rail, so that the pressing plate can tightly press the mounting desktop. After the rotating pipe is rotated, the threaded pipe is driven to rotate and move through threaded engagement, so that the pressing block is driven to move. The pressing block is matched with the pressing plate, so that the main body can be mounted on the edge of the desktop for use without occupying the use space of the desktop.

In addition, after the clamping band crosses through the inside of the clamping groove, the rotating wheel drives the driving wheel to rotate. The adjusting wheel is meshed with the driving wheel so that the adjusting wheel rotates. The adjusting wheel is meshed with the clamping strip to drive the clamping band to adjust the tightness. The gap between the wrist and the clamping band is filled by the protection ring, so that the connecting cover is prevented from hurting the wrist, and the use comfort is ensured. The body temperature information collected by the clamping band is measured by the thermoelectric potential generated at the cold end and the working end, and the information is recorded and stored by the recording device.

BRIEF DESCRIPTION OF THE DRAWINGS

In order to explain the technical scheme of the embodiment of the present disclosure more clearly, the drawings of the embodiment will be briefly introduced hereinafter.

The drawings in the following description only relate to some embodiments of the present disclosure, rather than limit the present disclosure.

In the Figures:

FIG. 1 shows a schematic diagram of the left front structure before use according to the present disclosure.

FIG. 2 shows a schematic diagram of the right rear structure before use according to the present disclosure.

FIG. 3 shows a schematic diagram of the left rear structure when using according to the present disclosure.

FIG. 4 shows a schematic diagram of the lower structure when using according to the present disclosure.

FIG. 5 show a schematic diagram of a partial cross-sectional structure of a moving pallet according to the present disclosure.

FIG. 6 show a schematic diagram of a partial cross-sectional structure of a recording device according to the present disclosure.

FIG. 7 show a structural schematic diagram of a fastener according to the present disclosure.

FIG. 8 shows an enlarged structural schematic diagram at A in FIG. 5 according to the present disclosure.

FIG. 9 shows an enlarged structural schematic diagram at B in FIG. 6 according to the present disclosure.

FIG. 10 shows an enlarged structural schematic diagram at C in FIG. 3 according to the present disclosure.

LIST OF REFERENCE NUMERALS

Figure 1:
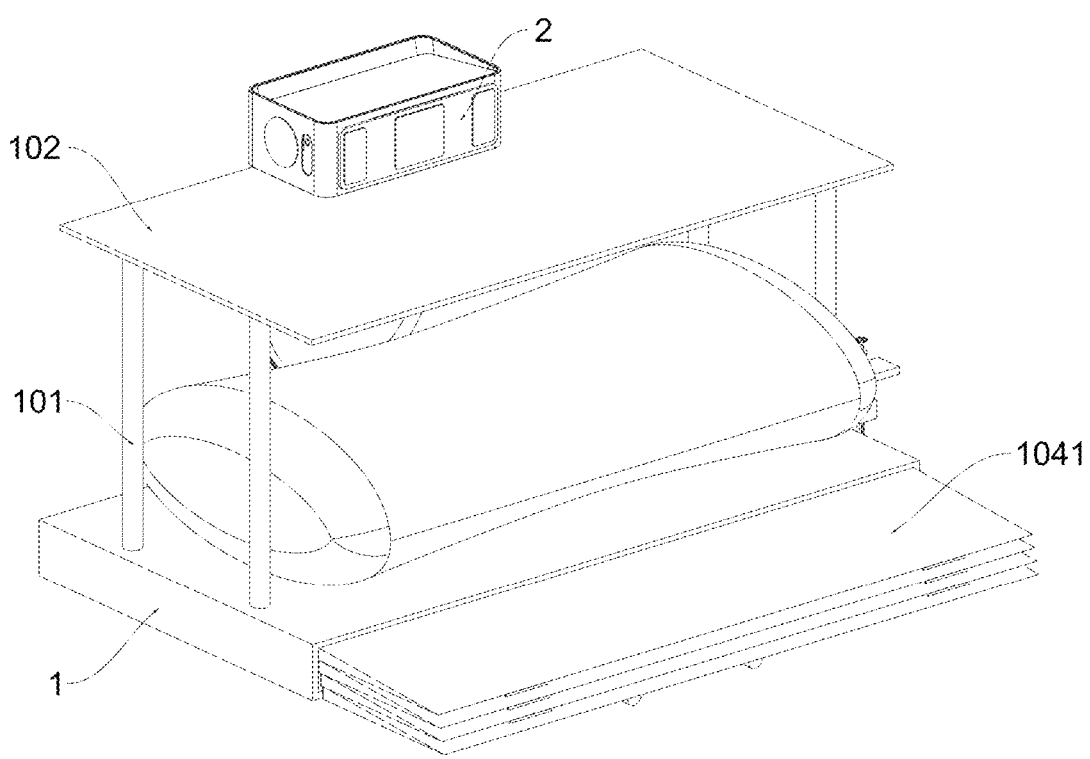
Figure 2:
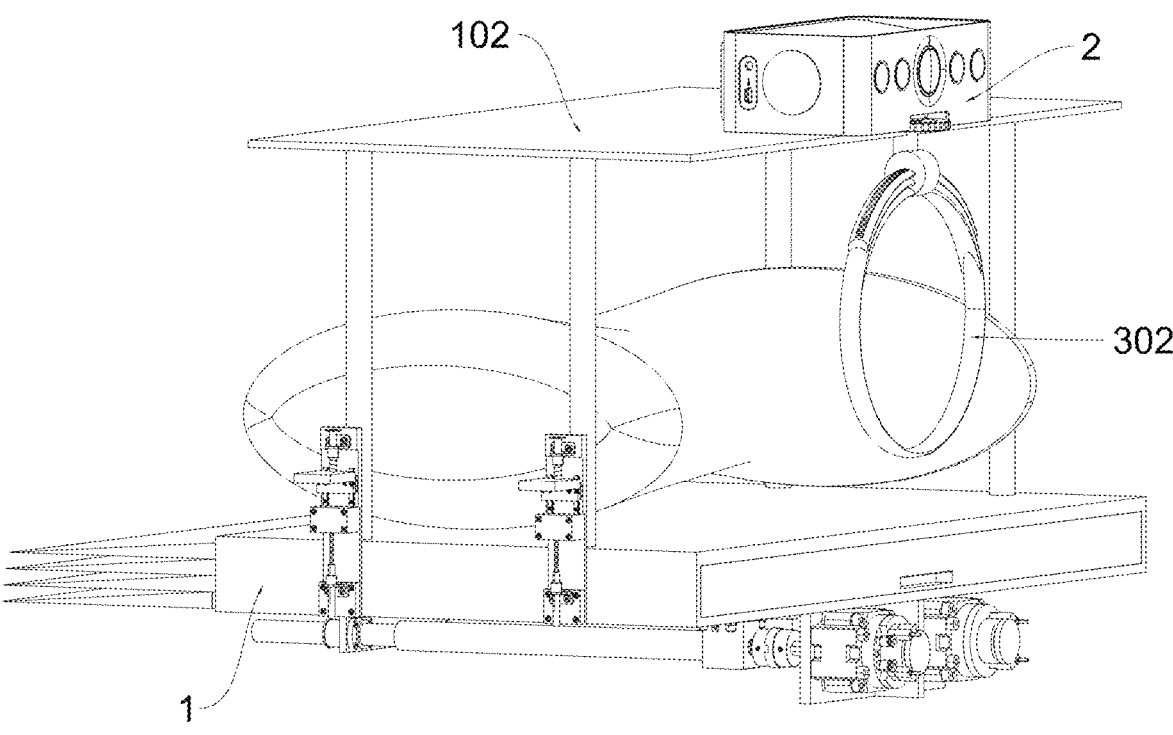

1. Main body; 101. Support rod; 102. Platform; 103. Drawer; 104. Pallet assembly; 1041. Connecting pallet; 10411. Towbar; 10412. Abutting plate; 1042. Moving pallet; 2. Recording device; 201. Display screen; 202. Rotary knob; 203. Rotating wheel; 2031. Driving wheel; 204. Connecting cover; 2041. Adjusting wheel; 2042. Clamping groove; 2043. Mounting groove; 3. Clamping band; 301. Clamping strip; 302. Protection ring; 4. Moving device; 401. Connecting plate; 402. Telescopic rod; 403. Fixed block; 404. Driving plate; 5. Fastener; 501. Fastening pipe; 502. Pressing plate; 503. Bearing plate; 504. Sliding rail; 6. Rotating pipe; 601. Threaded pipe; 602. Pressing block.

DETAILED DESCRIPTION OF THE EMBODIMENTS

In order to make the purpose, scheme and advantages of the technical scheme of the present disclosure clearer, the technical scheme of the embodiment of the present disclosure will be described clearly and completely in conjunction with the attached drawings of specific embodiments of the present disclosure hereinafter. Unless otherwise specified, the terms used herein have the ordinary meaning in the art. Like reference numerals in the drawings represent like parts.

Embodiment: please refer to FIG. 1 to FIG. 10.

The present disclosure provides a steerable and adjustable recorder pulse pillow for Traditional Chinese Medicine pulse diagnosis, comprising a main body 1. A pulse pillow is placed above the main body 1. A platform 102 is installed right above the main body 1. A pallet assembly 104 is movably connected inside the main body 1. A fastener 5 is fixedly connected to the right end of the main body 1. A moving device 4 is fixedly connected to the bottom surface of the main body 1. The platform 102 has a rectangular structure and has a recording device 2 installed on the top surface. The bottom of the recording device 2 is provided with a rotary disc. The rear end surface of the recording device 2 is provided with an operating button. The rotary disc is fixedly connected with a micro-motor driving wheel inside the recording device 2. The micro-motor is electrically connected with a rotary knob 202 of the recording device 2. The bottom of the recording device 2 is movably clamped with a rotating wheel 203. The bottom of the rotating wheel 203 is fixedly connected with a connecting cover 204. The connecting cover 204 is internally clamped with a clamping band 3 and a protection ring 302. A connecting plate 401 included in the moving device 4 is fixedly connected to the bottom surface of the pallet assembly 104. A driving block 404 included in the moving device 4 is fixedly connected to the bottom surface of the main body 1. A driver is installed at the rear end of the driving block 404. The driver is electrically connected with the operating button of the recording device 2. The left end of the fastener 5 is fixedly connected with a bearing plate 503 and a sliding rail 504. The left end of the bearing plate 503 is fixedly connected with a rotating pipe 6. The left side of the sliding rail 504 is slidably clamped with the pressing block 602.

Figure 9:
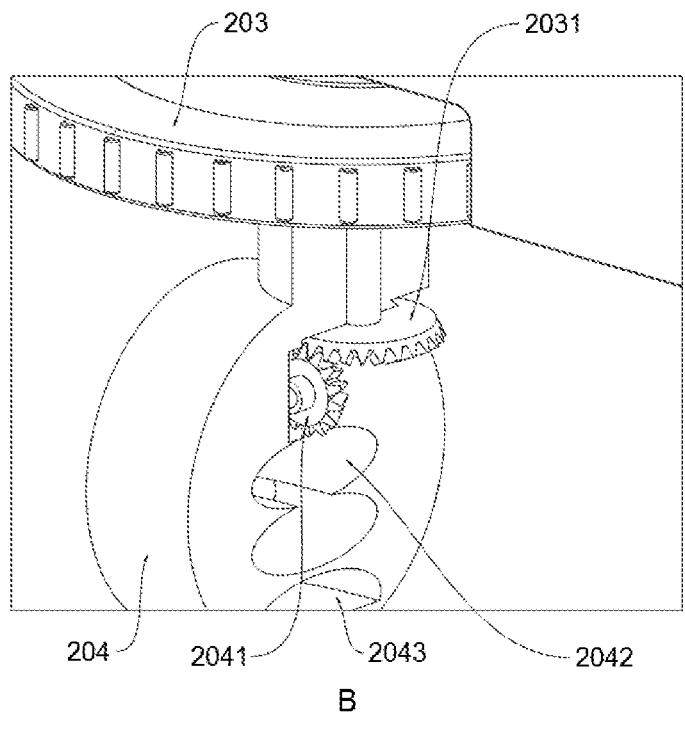

In addition, according to the embodiment of the present disclosure, as shown in FIG. 9, the connecting cover 204 comprises an adjusting wheel 2041, a clamping groove 2042 and a mounting groove 2043. The adjusting wheel 2041 has a bevel gear structure and is meshed with the driving wheel 2031. The outside of the clamping groove 2042 has an 8-shaped structure and the inside of the clamping groove is installed with a clamping band 3. The mounting groove 2043 is provided below the clamping groove 2042. The inside of the mounting groove 2043 is clamped with the protection ring 302. After the clamping band 3 crosses through the inside of the clamping groove 2042, the rotating wheel 203 can drive the driving wheel 2031 to rotate. The adjusting wheel 2041 is meshed with the driving wheel 2031 so that the adjusting wheel 2041 adjusts the tightness of the clamping band 3.

Figure 7:
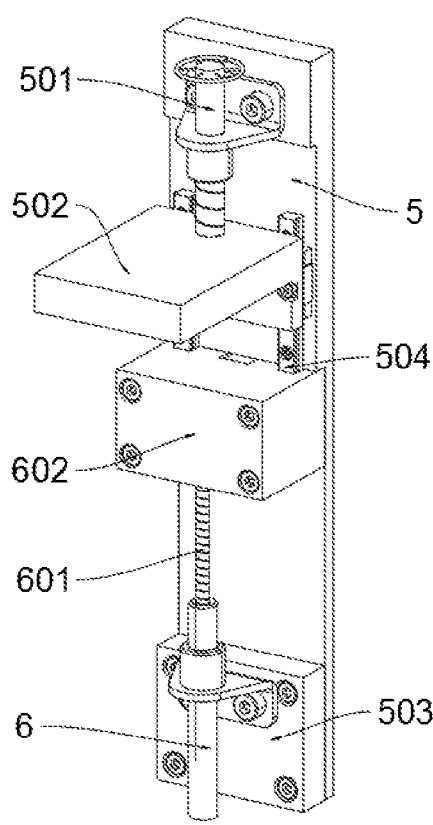

In addition, according to the embodiment of the present disclosure, as shown in FIG. 7, the rotating pipe 6 comprises a threaded pipe 601. The threaded pipe 601 is movably connected in the rotating pipe 6 through threaded engagement, and the top surface of the threaded pipe 601 is movably clamped in the pressing block 602. After the rotating pipe 6 is rotated, the threaded pipe 601 is driven to rotate and move through threaded engagement, so that the pressing block 602 is driven to move. The pressing block 602 is matched with the pressing plate 502, so that the main body 1 can be mounted on the edge of the desktop, which is convenient to use without affecting the original use space of the desktop.

Figures 3, 4:
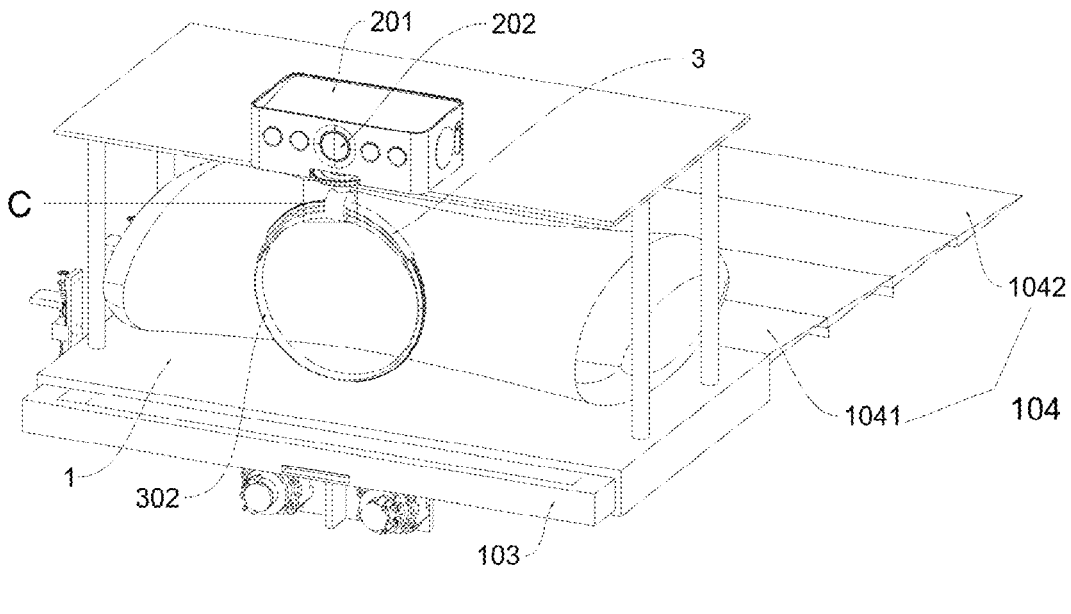

In addition, according to the embodiment of the present disclosure, as shown in FIG. 4, the moving device 4 further comprises a telescopic rod 402 and a fixed block 403. The front end of the telescopic rod 402 is fixedly connected with the front end surface of the connecting plate 401. The rear end of the telescopic rod 402 is fixedly connected with the driving block 404. The periphery of the rear side of the telescopic rod 402 is fixedly connected with the fixed block 403. The top surface of the fixed block 403 is fixedly connected with the bottom surface of the main body 1 through a bolt assembly. After the driver at the rear end of the driving block 404 is started by the operating button of the recording device 2, the telescopic rod 402 is pushed to extend forward, which drives the connecting plate 401 to move forward and also drives the moving pallet 1042 to move forward.

In addition, according to the embodiment of the present disclosure, as shown in FIGS. 1 and 3, the main body 1 comprises a support rod 101 and a drawer 103. The support rod 101 is fixed and vertically connected to the top surface of the main body 1. The top surface of the support rod 101 is fixedly connected to the bottom surface of the platform 102, and the drawer 103 is movably clamped in the main body 1. When the pallet assembly 104 is folded to the innermost position, the front end surface of the drawer 103 is attached to the rear end surface of the pallet assembly 104. The drawer 103 can be used to accommodate medical articles such as silver needles, disinfecting swabs, alcohol cloth, etc. The support rod 101 provides a supporting foundation for the platform 102 and further provides a space into which a pulse pillow is placed.

Figure 5:
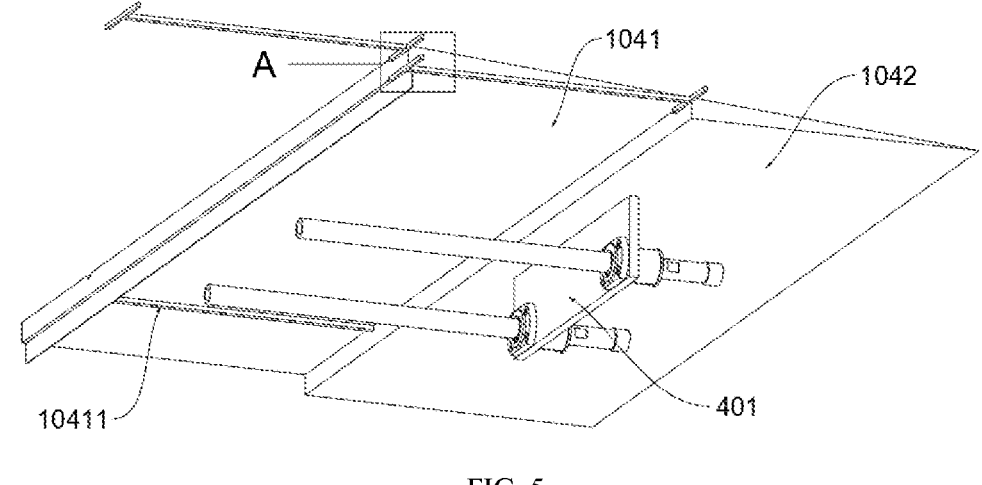
Figure 6:
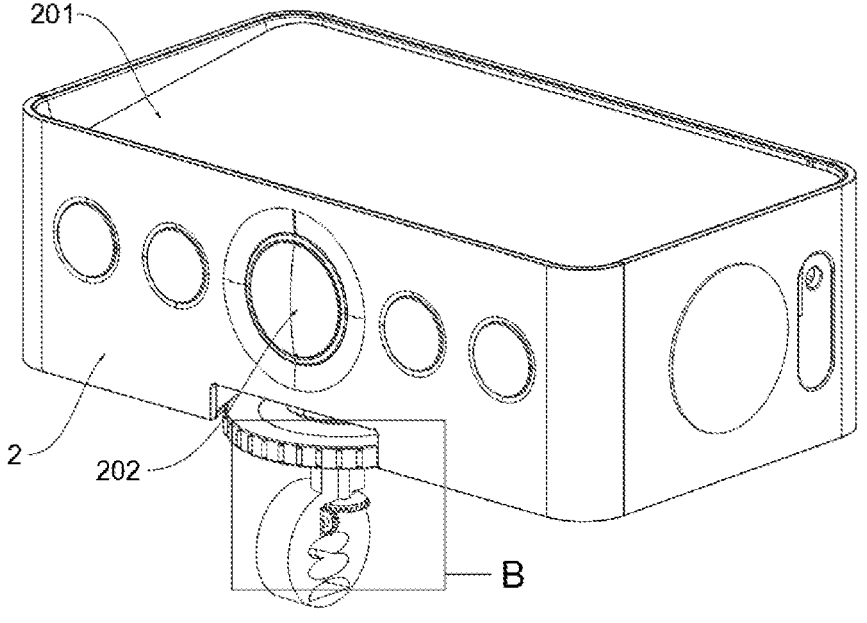
Figure 8:
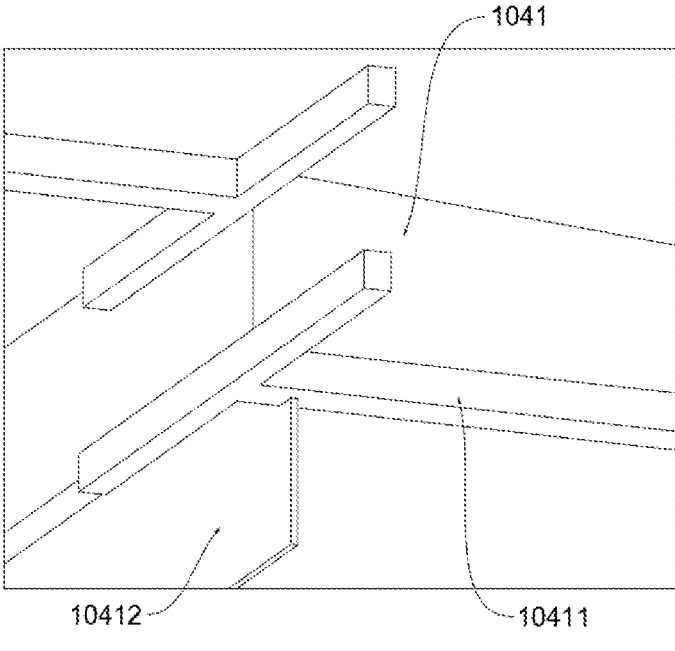

In addition, according to the embodiment of the present disclosure, as shown in FIG. 3, FIG. 5 and FIG. 8, the pallet assembly 104 consists of a connecting pallet 1041 and a moving pallet 1042. The pallet assembly 104 has three groups of connecting pallets 1041 with the same structure. The rear end surfaces of the connecting pallet 1041 and the moving pallet 1042 are fixedly connected with towbars 10411 with I-shaped structures, respectively. The rear end of the bottom surface of the connecting pallet 1041 is fixedly connected with an abutting plate 10412. The middle longitudinal beam of the towbar 10411 penetrates through the abutting plate 10412, and the rear cross beam of the towbar 10411 is clamped at the rear side of the abutting plate 10412. When the moving pallet 1042 moves forward and stretches, the towbar 10411 on the bottom surface of the moving pallet 1042 is driven to move forward and slide inside a group of adjacent abutting plates 10412 at the bottom surface of the connecting pallet 1041. After the towbar 10411 moves to the rear cross beam and abuts against the rear end surface of the abutting plate 10412, the towbar 10411 drives the abutting plate 10412 to move and also drives the connecting pallet 1041 to move forward, so as to finally complete the stretch of the pallet assembly 104. When the moving pallet 1042 moves backward and folds, the towbar 10411 at the bottom surface of the moving pallet 1042 is driven to move backward and slide inside a group of adjacent abutting plates 10412 at the bottom surface of the connecting pallet 1041. After the front cross beam of the towbar 10411 abuts against the front end surface of the abutting plate 10412, the towbar 10411 drives the abutting plate 10412 to move backward and also drives the connecting pallet 1041 to move backward, so as to finally complete the folding of the pallet assembly 104.

In addition, according to the embodiment of the present disclosure, as shown in FIG. 3, the top surface of the recording device 2 is provided with a display screen 201. The display screen 201 is connected with a PLC controller and a CPU chip circuit inside the recording device 2, and the display screen 201 is electrically connected with the operating button. After a recording device 2 records the physical sign information such as body temperature, pulse, and heart rate of a patient, the information is recorded and stored through the operating button, and a real-time picture is displayed through a display screen 201. The rotating direction and angle of the micro-motor can be adjusted by the rotary knob 202 according to the sitting position of a patient, the rotating angle of the recording device 2 is then driven through the rotary disc, so that both the patient and the doctor can watch the picture of the display screen 201 through steering adjustment.

In addition, according to the embodiment of the present disclosure, as shown in FIG. 9, the rotating wheel 203 comprises a driving wheel 2031. The driving wheel 2031 has a bevel gear structure and is movably clamped at the bottom of the rotating wheel 203. The driving wheel 2031 is coaxially and fixedly connected with the rotating wheel 203. The driving wheel 2031 is driven to rotate when the rotating wheel 203 rotates to provide power for adjusting the tightness of the clamping band 3.

In addition, according to the embodiment of the present disclosure, as shown in FIG. 7, the left end of the fastener 5 is further provided with a fastening pipe 501. The fastening pipe 501 has a threaded sleeve structure. The outer pipe at the upper end of the fastening pipe is movably clamped at the upper end of the left side of the fastener 5. The inner pipe at the lower end of the fastening pipe 501 is movably clamped with a pressing plate 502. The pressing plate 502 has a right-angle structure and is movably clamped to the left side of the sliding rail 504. After the fastening pipe 501 is rotated, the inner pipe at the lower end is driven to rotate and move, and the pressing plate 502 is driven to slide on the left side of the sliding rail 504, so that the pressing plate 502 can tightly press the mounting desktop.

Figure 10:
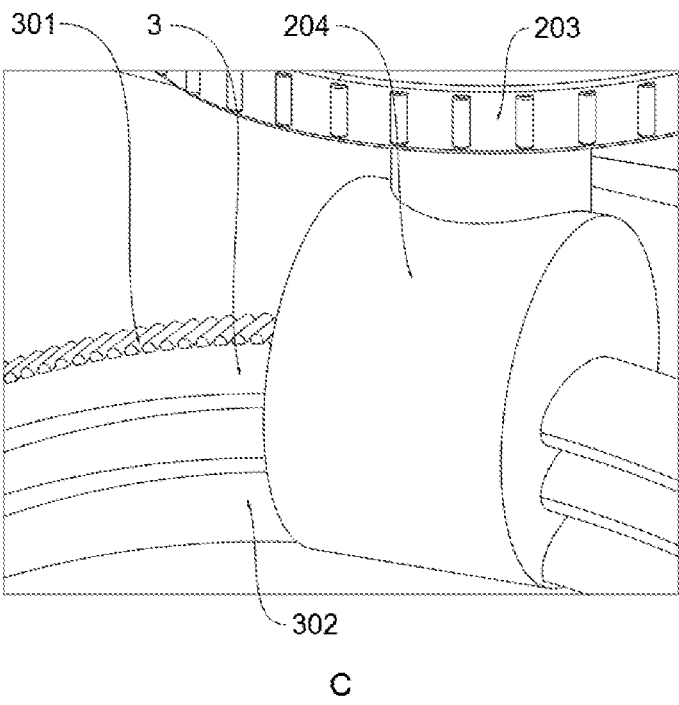

In addition, according to the embodiment of the present disclosure, as shown in FIG. 10, a clamping strip 301 is provided at the outer side of the end of the clamping band 3. The clamping strip 301 is meshed with the adjusting wheel 2041. The inner side surface of the clamping band 3 is attached to the outer side surface of the protection ring 302. The clamping band 3 is the cold end of a thermocouple thermometer and is communicated with the internal working end of the recording device 2. The clamping strip 301 is used so that the clamping band 3 can adjust the tightness through the adjusting wheel 2041. The gap between the wrist and the clamping band 3 is filled by the protection ring 302, so that the connecting cover 204 is prevented from hurting the wrist, and the use comfort is ensured. The body temperature information collected by the clamping band 3 is recorded and stored by the recording device 2.

The specific usage and function of the embodiment are as follows. In the present disclosure, after the fastening pipe 501 is rotated, the inner pipe at the lower end is driven to rotate and move, and the pressing plate 502 is driven to slide on the left side of the sliding rail 504, so that the pressing plate 502 can tightly press the mounting desktop. After the rotating pipe 6 is rotated, the threaded pipe 601 is driven to rotate and move through threaded engagement, so that the pressing block 602 is driven to move. The pressing block 602 is matched with the pressing plate 502, so that the main body 1 can be mounted on the edge of the desktop for use.

After the driver at the rear end of the driving block 404 is started by the operating button of the recording device 2, the telescopic rod 402 is pushed to extend forward, which drives the connecting plate 401 to move forward and also drives the moving pallet 1042 to move forward. The towbar 10411 on the bottom surface of the moving pallet 1042 moves forward and slides inside a group of adjacent abutting plates 10412 at the bottom surface of the connecting pallet 1041. After the towbar 10411 moves to the rear cross beam and abuts against the rear end surface of the abutting plate 10412, the towbar

10411 drives the abutting plate 10412 to move and also drives the connecting pallet 1041 to move forward, so as to finally complete the stretch of the pallet assembly 104.

After the clamping band 3 crosses through the inside of the clamping groove 2042, the rotating wheel 203 is rotated to drive the driving wheel 2031 to rotate. The adjusting wheel 2041 is meshed with the driving wheel 2031 so that the adjusting wheel 2041 rotates. The adjusting wheel 2041 is meshed with the clamping strip 301 to drive the clamping band 3 to adjust the tightness. The gap between the wrist and the clamping band 3 is filled by the protection ring 302, so that the connecting cover 204 is prevented from hurting the wrist, and the use comfort is ensured.

Finally, it should be noted that the present disclosure usually takes one/a pair of components as an example when describing the positions of various components and the mating relationship between them. However, it should be understood by those skilled in the art that such positions, mating relationships, etc. are also applicable to other components/other paired components.

The above is only an exemplary embodiment of the present disclosure, rather than limit the scope of protection of the present disclosure. The scope of protection of the present disclosure is determined by the appended claims.

What is claimed is:

1. A steerable and adjustable recorder pulse pillow for Traditional Chinese Medicine pulse diagnosis, comprising:
   a main body;
   the pulse pillow placed on the main body;
   a platform disposed right above the main body;
   a pallet assembly movably connected inside the main body;
   a fastener fixedly connected to a right end of the main body; and
   a moving device fixedly connected to a bottom surface of the main body;
   wherein the platform has a rectangular structure, a recording device is installed on a top surface of the platform; a rear end surface of the recording device is provided with an operating button and a rotary knob, and a bottom portion of the recording device is movably clamped with a rotating wheel;
   wherein a bottom of the rotating wheel is fixedly connected with a connecting cover, the connecting cover is internally clamped with a clamping band and a protection ring, a connecting plate included in the moving device is fixedly connected to a bottom surface of the pallet assembly, and a driving block included in the moving device is fixedly connected to the bottom surface of the main body;
   wherein a left end of the fastener is fixedly connected with a bearing plate and a sliding rail, the left end of the bearing plate is fixedly connected with a rotating pipe, and a left side of the sliding rail is slidably clamped with a pressing block.

2. The steerable and adjustable recorder pulse pillow of claim 1, wherein the main body comprises a support rod and a drawer, the support rod is fixed and vertically connected to a top surface of the main body, a top surface of the support rod is fixedly connected to a bottom surface of the platform, and the drawer is movably clamped in the main body.

3. The steerable and adjustable recorder pulse pillow of claim 1, wherein the pallet assembly consists of three groups of connecting pallets with a same structure and a moving pallet, a rear end surface of each connecting pallet and the moving pallet in each group of the three groups of connecting pallets are fixedly connected with towbars with I-shaped structures, respectively, a rear end of a bottom surface of each connecting pallet is fixedly connected with an abutting plate, a middle longitudinal beam of the towbar penetrates through the abutting plate, and a rear cross beam of the towbar is clamped at a rear side of the abutting plate.

4. The steerable and adjustable recorder pulse pillow of claim 1, wherein a top surface of the recording device is provided with a display screen, the display screen is connected with a programmable logic controller (PLC) and a central processing unit (CPU) chip circuit inside the recording device, and the display screen is electrically connected with the operating button.

5. The steerable and adjustable recorder pulse pillow of claim 1, wherein the rotating wheel comprises a driving wheel, the driving wheel has a bevel gear structure and is movably clamped at the bottom of the rotating wheel, and the driving wheel is coaxially and fixedly connected with the rotating wheel.

6. The steerable and adjustable recorder pulse pillow of claim 1, wherein the connecting cover comprises an adjusting wheel, a clamping groove and a mounting groove, wherein the adjusting wheel has a bevel gear structure and is meshed with a driving wheel, an outside of the clamping groove has an 8-shaped structure and an inside of the clamping groove is installed with the clamping band, the mounting groove is provided below the clamping groove, and an inside of the mounting groove is clamped with the protection ring.

7. The steerable and adjustable recorder pulse pillow of claim 6, wherein a clamping strip is provided at an outer side of an end of the clamping band, the clamping strip is meshed with the adjusting wheel, an inner side surface of the clamping band is attached to an outer side surface of the protection ring, and the clamping band is a cold end of a thermocouple thermometer and is communicated with an internal working end of the recording device.

8. The steerable and adjustable recorder pulse pillow of claim 1, wherein the moving device further comprises a telescopic rod and a fixed block, a front end of the telescopic rod is fixedly connected with a front end surface of the connecting plate, a rear end of the telescopic rod is fixedly connected with the driving block, a periphery of a rear side of the telescopic rod is fixedly connected with the fixed block, and a top surface of the fixed block is fixedly connected with the bottom surface of the main body through a bolt assembly.

9. The steerable and adjustable recorder pulse pillow of claim 1, wherein the left end of the fastener is further provided with a fastening pipe, the fastening pipe has a threaded sleeve structure, an outer pipe at an upper end of the fastening pipe is movably clamped at an upper end of the left side of the fastener, an inner pipe at a lower end of the fastening pipe is movably clamped with a pressing plate, and the pressing plate has a right-angle structure and is movably clamped to the left side of the sliding rail.

10. The steerable and adjustable recorder pulse pillow of claim 1, wherein the rotating pipe comprises a threaded pipe, the threaded pipe is movably connected in the rotating pipe through threaded engagement, and a top surface of the threaded pipe is movably clamped in the pressing block.

* * * * *